United States Patent [19]

Pastor et al.

[11] Patent Number: 5,013,510
[45] Date of Patent: May 7, 1991

[54] PROCESS FOR PREPARING LONG CHAIN N,N-DIALKYLHYDROXYLAMINES BY DIRECT OXIDATION

[75] Inventors: Stephen D. Pastor, Danbury, Conn.; Paul A. Odorisio, Edgewater, N.J.

[73] Assignee: Ciba-Geigy Corporation, Ardsley, N.Y.

[21] Appl. No.: 366,974

[22] Filed: Jun. 14, 1989

Related U.S. Application Data

[63] Continuation-in-part of Ser. No. 947,003, Dec. 29, 1986, abandoned.

[51] Int. Cl.$^5$ .............................................. C07C 239/10
[52] U.S. Cl. ...................................... 564/301; 564/300
[58] Field of Search ................................ 564/300, 301

[56] References Cited

U.S. PATENT DOCUMENTS

| | | | |
|---|---|---|---|
| 3,243,462 | 3/1966 | Smith | 564/301 |
| 4,845,290 | 7/1989 | Legrand et al. | 564/300 |
| 4,876,300 | 10/1989 | Seltzer et al. | 524/102 X |
| 4,898,901 | 2/1990 | Ravichandran et al. | 524/237 |

OTHER PUBLICATIONS

R. W. Murray et al., Synthetic Communications, 19, 3509, (1989).
S-I Murahashi et al., J. Org. Chem., 1990, 55, 1736.

*Primary Examiner*—Richard L. Raymond
*Attorney, Agent, or Firm*—Luther A. R. Hall

[57] ABSTRACT

N,N-Dialkylhydroxylamines where the alkyl groups are of 10 to 30 carbon atoms are prepared by an improved process involving the direct oxidation of the corresponding N,N-dialkylamines with aqueous hydrogen peroxide in a lower alkanol solvent in the absence of a catalyst or a sequestering agent.

The improved process prevents the problem of overoxidation and gives the desired N,N-dialkylhydroxylamine in high yield and purity. The N,N-dialkylhydroxylamines are effective stabilizers for polymer compositions particularly as process stabilizers for polyolefins.

7 Claims, No Drawings

PROCESS FOR PREPARING LONG CHAIN N,N-DIALKYLHYDROXYLAMINES BY DIRECT OXIDATION

This is a continuation-in-part application of application Ser. No. 947,003, filed on Dec. 29, 1986 now abandoned.

This invention pertains to an improved process for preparing long chain N,N-dialkylhydroxylamines.

BACKGROUND OF THE INVENTION

Long chain N,N-dialkylhydroxylamines are effective in stabilizing polyolefin compositions against thermal degradation, as is seen in U.S. Pat. No. 4,590,231, particularly as processing stabilizers in the presence of phenolic antioxidants and/or other costabilizers.

N,N-Dialkylhydroxylamines have been discussed periodically in the prior art, and several reviews of the general methods of their preparation are available. These are notably S. Wawzonek et al, Organic Preparations and Procedures Int. 4(3), 135 (1972); and J. S. Roberts, Comprehensive Organic Chem., Ed. Sir D. Barton and W.D. Ollis, Chapter 6.4, p.185 (1979). Both of these reviews point out the facile Cope reaction involving the pyrolysis of an amine oxide to give an olefin and concomitantly a hydroxylamine.

Wawzonek et al describe the direct oxidation of secondary dialkylamines to the corresponding hydroxylamines using hydrogen peroxide, but point out the over-oxidation, low yields and other difficulties encountered.

British Patent No. 1,134,851 describes preparing N,N-dialkylhydroxylamines by oxidizing a tertiary amine with hydrogen peroxide to form the N-oxide in the presence of water, removing the water by azeotropic distillation and pyrolyzing the residue to form an olefin and the hydroxylamine.

A. C. Cope et al, Organic Reactions, Vol 11, Chapter 5, 317 (1960) describes the preparation of olefins from amines, the Hofmann elimination reaction and the pyrolysis of amine oxides. Emphasis is placed on the structure of the olefins prepared and N,N-di(lower alkyl)hydroxylamines are the hydroxylamines discussed.

U.S. Pat. No. 3,274,252 discloses the process for the aqueous oxidation of a tri(lower alkyl)amine with hydrogen peroxide in the presence of an alkali metal tungstate catalyst and alkali metal pyrophosphate to give the corresponding amine oxide followed by pyrolysis of the aqueous reaction mass to give the corresponding N,N-di(lower alkyl)hydroxylamine.

U.S. Pat. No. 3,709,942 discusses the preparation of N,N-dimethylhydroxylamine by the pyrolysis of aqueous alkyldimethylamine oxide.

U.S. Pat. No. 3,293,034 describes the preparation of various N,N-di(lower alkoxyalkyl)hydroxylamines by the oxidation of the corresponding secondary amine with hydrogen peroxide. Control of the reaction is difficult and the products are isolated by vacuum distillation in low yields.

U.S. Pat. Nos. 3,467,711 and 3,655,764 describe a process for preparing various N,N-di(lower alkoxyalkyl)hydroxylamines by the oxidation of the corresponding secondary amine with aqueous hydrogen peroxide in the presence of a metal sequestering agent such as ethylene diamine tetraacetic acid.

M.A.T. Rogers, J. Chem. Soc., 1955, 769 describes the preparation of N,N-dialkylhydroxylamines by a reverse Michael reaction on the N-oxides of the corresponding $\beta$-dialkylaminopropionic esters or nitriles or selected Mannich bases under alkaline conditions. Said N-oxides are prepared by oxidation of the corresponding $\beta$-dialkylamino compounds using monoperphthalic acid.

Rogers also describes the pyrolysis of tertiary amine oxides to give N,N-dialkylhydroxylamines.

Further Rogers points out that the direct oxidation of secondary amines by hydrogen peroxide is quite unsuitable which is not surprising in view of the strong reducing properties of hydroxylamines which are formed in the presence of hydrogen peroxide.

U.S. Pat. No. 3,243,462 describes the oxidation of lower dialkylamines to the corresponding lower dialkylhydroxylamines with hydrogen peroxide in the presence of a catalyst such as sodium tungstate or sodium vanadate. Only low yields of dialkylhydroxylamines are obtained.

OBJECT OF THE INVENTION

The object of the instant invention is to provide an improved process for preparing long chain N,N-dialkylhydroxylamines which avoids the problem of over-oxidation of the reaction product and which provides a facile method for the isolation of product of high yield and purity.

ADVANTAGES OF THE INSTANT INVENTION

The instant invention pertains to an improved process for making long chain N,N-dialkylhydroxylamines which has a number of advantages over the processes of the prior art.

These are:

1. The specific conditions employed in the present process preclude the problem of over-oxidation of the long chain N,N-dialkylhydroxylamine commonly associated with the preparation of N,N-dialkylhydroxylamines by powerful oxidants such as hydrogen peroxide.

2. The instant process permits the facile isolation of the N,N-dialkylhydroxylamine from the reaction medium containing hydrogen peroxide by filtration since the desired product is insoluble in the reaction medium and separates therefrom. This not only protects it from unwanted over-oxidation, but facilitates the isolation of the product in high yield and in high purity avoiding the costly and tedious procedures of pyrolysis, distillation and/or extraction.

3. The process is carried out under mild and non-rigorous conditions at a temperature of 40 to 65° C., preferably at 50–60° C. This clearly has beneficial features of reduced energy costs associated with the high temperature amine oxide pyrolysis method.

4. The process is a direct one-step process avoiding the necessity of isolating any intermediate and carrying out a separate second step thereon.

DETAILED DISCLOSURE

The instant invention is an improved process for the preparation of a long chain N,N-dialkylhydroxylamines which comprises oxidizing a secondary dialkylamine of the formula $E_1E_2NH$ wherein $E_1$ and $E_2$ are independently alkyl of 10 to 30 carbon atoms, with aqueous hydrogen peroxide solution at a temperature of 40 to 65° C. to give the corresponding N,N-dialkylhydroxylamine $E_1E_2NOH$ wherein the improvement comprises
dissolving the secondary dialkylamine $E_1E_2NH$ in a lower alkanol solvent,
oxidizing said dialkylamine with a molar excess of 10–70% aqueous hydrogen peroxide to form the N,N-dialkylhydroxylamine $E_1E_2NOH$ which precipitates from the aqueous lower alkanol reaction medium, and
isolating the insoluble N,N-dialkylhydroxylamine, said process being carried out in the absence of a catalyst or of a sequestering agent.

The dialkylamines are largely items of commerce or can be prepared by conventional methods.

$E_1$ and $E_2$ are independently alkyl of 10 to 30 carbon atoms where the alkyl is for example decyl, dodecyl, tridecyl, tetradecyl, hexadecyl, octadecyl, eicosyl or tricontyl.

Preferably $E_1$ and $E_2$ are dodecyl, tetradecyl, hexadecyl, the alkyl mixture found in hydrogenated tallow amine or octadecyl.

Most preferably $E_1$ and $E_2$ are the alkyl mixture found in the hydrogenated tallow amine.

A typical di(hydrogenated tallow)amine has the following distribution of alkyl substituents:

| | $E_1E_2NH$ | |
| --- | --- | --- |
| $E_1$ | $E_2$ | % |
| $C_{16}$ | $C_{14}$ | 1.9 |
| $C_{16}$ | $C_{16}$ | 12.4 |
| $C_{16}$ | $C_{17}$ | 2.8 |
| $C_{16}$ | $C_{18}$ | 36.0 |
| $C_{17}$ | $C_{18}$ | 3.9 |
| $C_{18}$ | $C_{18}$ | 39.0 |
| | other | 4.0 |

It is clear that the di(hydrogenated tallow)amine originating from animal sources may well vary somewhat in the specific distribution of alkyl substituents, but the di(hydrogenated tallow)amine contains major amounts of di(hexadecyl)amine, di(octadecyl)amine and N-hexadecyl-N-octadecylamine.

The instant process is carried out under mild conditions at a temperature of 40 to 65° C., preferably at 50–60° C.

The oxidant in the instant process is 10 to 70% aqueous hydrogen peroxide, preferably a 50 to 70% aqueous hydrogen peroxide solution. A molar excess of hydrogen peroxide can be used to assure complete conversion of the secondary amine to the corresponding N,N-dialkylhydroxylamine without fear of over-oxidation of the product.

The key aspect of the instant invention upon which the improved process is focused involves a facile method of preventing over-oxidation of the N,N-dialkylhydroxylamine formed. This occurs because of the relative solubilities of the starting secondary dialkylamine and the product formed during the oxidation reaction when it is carried out in an aqueous lower alkanol reaction medium.

The secondary dialkylamine is soluble in the reaction medium, but the corresponding long-chain N,N-dialkylhydroxylamine formed is insoluble in the reaction medium and precipitates from the reaction medium as it is formed.

This precipitation of desired product not only protects said product from unwanted over-oxidation problems, but also facilitates its isolation and purification.

The instant N,N-dialkylhydroxylamines are obtained in high yield and purity by mere filtration of the reaction mixture. Still further purification by recrystallization can be carried out if needed.

It is thus clear that the choice of reaction medium is critical for the benefits of the instant improved product to be achieved. The important criteria are solubility of long chain secondary dialkylamine in the reaction medium and the concomitant insolubility of the corresponding N,N-dialkylhydroxylamine in the same reaction medium. There will clearly be some minor variation in choice of reaction medium depending on which specific long chain dialkylamine is used.

Since aqueous hydrogen peroxide solution is used as the oxidant and since water is present from this source as well as the by-product of the oxidation itself, a solvent with at least some water miscibility or solubility is desirable.

The lower alkanols are the reaction medium solvents of choice such as methanol, ethanol, n-propanol, isopropanol, n-butanol, isobutanol, sec-butanol and tert-butanol. The preferred solvents are ethanol, n-butanol and tert-butanol. Ethanol is a particularly preferred solvent.

In addition, the butyl alcohols, particularly n-butanol, provide a unique balance between water miscibility which is required to carry out the oxidation of the long chain N,N-dialkylamines while allowing for a convenient phase separation between the aqueous phase and the organic solvent phase of the reaction mixture. The phase separation facilitates recycling of the starting materials which may be recovered from the reaction filtrate.

The following examples are presented to illustrate the instant improved process without limiting the scope thereof in any manner whatsoever.

EXAMPLE 1

N,N-Di(hydrogenated tallow)hydroxylamine

Into a solution of 100 grams (0.18 mol) of di(hydrogenated tallow)amine (494 eq. wt., 90% secondary amine) in 400 ml of n-butanol at 55° C. is added 8.6 ml (0.22 mol) of 70% aqueous hydrogen peroxide solution. The reaction is complete when all the hydrogen peroxide is consumed as determined by titration of an aliquot of the reaction mixture with potassium iodide/sulfuric acid/sodium thiosulfate.

The above-named product is isolated from the reaction mixture by filtration. The filter cake is washed with two 50 ml portions of n-butanol at 55° C.; then dried to give the desired product in a yield of 63 grams (68%) as a white solid melting at 93–96° C.

EXAMPLE 2

N,N-Di(hydrogenated tallow)hydroxylamine

Following the general procedure of Example 1, to a solution of 52.6 grams (0.09 mol) of di(hydrogenated tallow)amine (526 eq. wt, 90% secondary amine) dissolved in 200 ml of n-butanol at 55° C. is added 5.3 ml (0.14 mol) of 70% aqueous hydrogen peroxide solution. During the course of the reaction three additional 0.5 ml (0.01 mol) portions of 70% aqueous hydrogen peroxide solution are added after 22, 24 and 72 hours.

The progress of the reaction is followed by thin layer chromatography (TLC) (silica gel; chloroform/acetic acid 98/2). The reaction is complete when all the starting amine has disappeared as determined by the TLC analysis.

The above-named product is isolated from the reaction mixture by filtration. The filter cake is washed with 100 ml of n-butanol at 55° C., and then with two 200 ml portions of methanol at ambient temperature to give the desired product in a yield of 27.6 grams (57%) as a white solid melting at 98–100° C.

EXAMPLE 3

N,N-Di(hydrogenated tallow)hydroxylamine

Following the general procedure of Example 1, to 200 grams (0.36 mol) of di(hydrogenated tallow)amine (494 eq. wt., 90% secondary amine) suspended in 800 ml of ethanol at 55° C. is added 29.4 ml (0.77 mol) of 70% aqueous hydrogen peroxide solution. After stirring for 18 hours at 55° C., the reaction mixture is filtered and the moist filter cake is recrystallized from 1000 ml of hexane. The recrystallized material is washed with 500 ml of hexane at 55° C. The above-named product is obtained in a yield of 123 grams (66%) as a white solid melting at 90–93° C.

EXAMPLE 4

This example illustrates the variety of conditions which may be useful in the oxidation of di(hydrogenated tallow)amine to N,N-di(hydrogenated tallow)hydroxylamine without over-oxidation to the corresponding nitrone.

A 25% wt/vol suspension of di(hydrogenated tallow)amine (494 eq. wt.; 90% secondary amine) in an alcohol solution is treated with the indicated equivalents of aqueous hydrogen peroxide solution and at the indicated temperature. After the indicated time, the reaction mixture is cooled and the product mixture isolated by filtration. The composition of the dried product mixture is determined by inspection of its XL 200 $^1$H NMR spectrum. The results are tabulated in Table I.

50% aqueous hydrogen peroxide solution and 400 ml of ethanol. After stirring for 48 hours, the reaction mixture is filtered to give the above-named product which is twice recrystallized from 500 ml of chloroform. The desired product is obtained in a yield of 29.4 grams (32%) as white needles melting at 97–99° C.

Analysis: Calcd for $C_{32}H_{67}NO$: C, 79.8; H, 14.0; N, 2.0.

Found: C, 79.5; H, 14.0; N, 2.7.

EXAMPLE 6

N,N-Di(dodecyl)hydroxylamine

Following the general procedure of Example 5, to a solution of 50 grams (0.14 mol) of didodecylamine dissolved in 200 ml of n-propanol at 40° C. is added dropwise 9.62 grams (0.14 mol) of 50% aqueous hydrogen peroxide solution. After 72 hours at 40–45° C., the reaction mixture is filtered to give a crude product which is subsequently recrystallized from 300 ml of hexane. The above-named product is obtained in a yield of 24.8 grams (48%) as white needles melting at 90–92° C.

Analysis: Calcd for $C_{24}H_{51}NO$: C, 78.0; H, 13.9; N, 3.8.

Found: C, 78.0; H, 14.2; N, 3.7.

EXAMPLE 7

N,N-Di(tetradecyl)hydroxylamine

The general procedure of Example 5 is followed using, at 50 to 55° C., 50 grams (0.12 mol) of ditetradecylamine, 200 ml of n-propanol and 8.3 grams (0.12 mol) of 50% aqueous hydrogen peroxide solution. The above-named product is obtained in a yield of 33.4 grams (64%) as white needles melting at 97–99° C.

EXAMPLE 8

N,N-Di(hydrogenated tallow)hydroxylamine

Into a warm solution of 49.5 grams of di(hydrogenated tallow)amine (494 eq. wt.; 90% secondary amine; 0.09 mol) in 200 ml of n-butanol at 54° to 55° C. is added 6.8 g (0.1 mol) of 50% aq. hydrogen peroxide solution. After 6 hours at 54° to 55° C., the reaction mixture is filtered through a fritted glass funnel while the reaction mass is warm. The reaction filtrate is allowed to cool and is diluted with 400 ml of methanol. A

TABLE I

| Alkanol | $H_2O_2$ | Temp. | Time | Relative Mole Ratio by $^1$H NMR* Hydroxylamine/Amine/Nitrone | | |
|---|---|---|---|---|---|---|
| Methanol | 2.1 | 60° C. | 24 hr. | 50 | 50 | <5 |
| Ethanol | 2.0 | 55° C. | 5 hr. | 50 | 50 | <5 |
| Isopropanol | 1.0 | 60° C. | 4 hr. | 40 | 60 | <5 |
| n-Butanol | 1.0 | 50° C. | 24 hr. | 70 | 30 | <5 |
| tert-Butanol | 1.0 | 65° C. | 48 hr. | 90 | 10 | <5 |

*Limits of detection are approximately 5 mol % and the value of less than 5 mol % is assigned to a component if it is not detected in the $^1$H NMR spectrum.

EXAMPLE 5

N,N-Di(hexadecyl)hydroxylamine

The general procedure of Example 3 is followed using 100 grams (0.19 mol) of di(hexadecyl)amine (451 eq. wt., 88% secondary amine), 30.2 grams (0.44 mol) of second crop is collected from the diluted filtrate. Finally, the reaction filtrate is diluted with 400 ml of water and a third crop is collected. The three reaction filter cakes are dried separately and analyzed by $^1$H NMR and LC. The results of the analysis are summarized in Table II.

TABLE II

| Reaction Filter Cake | Isolated Yield (g) | Calculated Yields from LC (g) Hydroxylamine/Amine/Nitrone | | | Calculated Yields from $^1$H NMR (g) Hydroxylamine/Amine/Nitrone | | |
|---|---|---|---|---|---|---|---|
| 1st | 32.5 | 23.1 | 7.2 | — | 26.5 | 5.9 | — |
| 2nd | 13.9 | 1.3 | 12.4 | — | — | 13.9 | — |
| 3rd | 3.1 | — | 0.71 | 0.56 | Undetermined | | |
| Total | 49.5 | 24.4 | 20.3 | 0.56 | 26.5 | 19.8 | — |
| Yield of Hydroxylamine | | 53% | | | 58% | | |
| Yield of Hydroxylamine (based upon recovered starting secondary amine) | | 97% | | | 96% | | |

What is claimed is:

1. An improved process for the preparation of a long chain N,N-dialkylhydroxylamine which comprises oxidizing a secondary dialkylamine of the formula $E_1E_2NH$ wherein $E_1$ and $E_2$ are independently alkyl of 10 to 30 carbon atoms, with aqueous hydrogen peroxide solution at a temperature of 40 to 65° C. to give the corresponding N,N-dialkylhydroxylamine $E_1E_2NOH$ wherein the improvement comprises
dissolving the secondary dialkylamine $E_1E_2NH$ in a lower alkanol solvent,
oxidizing said dialkylamine with a molar excess of 10–70% aqueous hydrogen peroxide to form the N,N-dialkylhydroxylamine $E_1E_2NOH$ which precipitates from the aqueous lower alkanol reaction medium, and
isolating the insoluble N,N-dialkylhydroxylamine, said process being carried out in the absence of a catalyst or of a sequestering agent.

2. A process according to claim 1 wherein $E_1$ and $E_2$ are dodecyl, tetradecyl, hexadecyl, the alkyl mixture found in hydrogenated tallow amine or octadecyl.

3. A process according to claim 1 wherein $E_1$ and $E_2$ are the alkyl mixture found in hydrogenated tallow amine.

4. A process according to claim 1 which is carried out at 50–60° C.

5. A process according to claim 1 wherein 50 to 70% aqueous hydrogen peroxide solution is used as an oxidant.

6. A process according to claim 1 wherein the lower alkanol solvent is ethanol, n-butanol or tert-butanol.

7. A process according to claim 1 wherein the lower alkanol solvent is ethanol.

* * * * *